United States Patent
Weber

(10) Patent No.: US 8,435,281 B2
(45) Date of Patent: May 7, 2013

(54) BIOERODIBLE, IMPLANTABLE MEDICAL DEVICES INCORPORATING SUPERSATURATED MAGNESIUM ALLOYS

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 191 days.

(21) Appl. No.: 12/421,928

(22) Filed: Apr. 10, 2009

(65) Prior Publication Data
US 2010/0262222 A1  Oct. 14, 2010

(51) Int. Cl.
*A61F 2/06* (2006.01)

(52) U.S. Cl.
USPC .................... 623/1.15; 623/16.11; 606/219

(58) Field of Classification Search ............... 623/11.11, 623/1.15, 16.11; 148/406; 606/219
See application file for complete search history.

(56) References Cited

U.S. PATENT DOCUMENTS

| | | | |
|---|---|---|---|
| 3,687,135 A | 8/1972 | Stroganov et al. | |
| 5,195,969 A | 3/1993 | Wang et al. | |
| 5,270,086 A | 12/1993 | Hamlin | |
| 5,366,504 A | 11/1994 | Andersen et al. | |
| 6,287,332 B1 | 9/2001 | Bolz et al. | |
| 6,726,712 B1 | 4/2004 | Raeder-Devens et al. | |
| 6,793,877 B1 | 9/2004 | Pettersen et al. | |
| 6,854,172 B2 | 2/2005 | Kaese et al. | |
| 6,908,516 B2 * | 6/2005 | Hehmann et al. | 148/406 |
| 7,011,678 B2 | 3/2006 | Tenerz et al. | |
| 7,067,606 B2 | 6/2006 | Mather et al. | |
| 7,651,527 B2 | 1/2010 | Krivoruchko et al. | |
| 2002/0004060 A1 | 1/2002 | Heublein | |
| 2003/0060873 A1 | 3/2003 | Gertner | |
| 2004/0034409 A1 | 2/2004 | Heublein | |
| 2004/0088038 A1 | 5/2004 | Dehnad | |
| 2004/0098108 A1 | 5/2004 | Harder | |
| 2004/0220660 A1 | 11/2004 | Shanley | |
| 2005/0038501 A1 | 2/2005 | Moore, Jr. | |
| 2005/0071016 A1 | 3/2005 | Hausdorf | |
| 2005/0234538 A1 | 10/2005 | Litvack | |
| 2005/0266041 A1 | 12/2005 | Gerold | |
| 2006/0052863 A1 | 3/2006 | Harder | |
| 2006/0052864 A1 | 3/2006 | Harder | |
| 2006/0198869 A1 | 9/2006 | Furst | |
| 2006/0212108 A1 | 9/2006 | Tittelbach | |
| 2006/0229711 A1 | 10/2006 | Yan | |

(Continued)

FOREIGN PATENT DOCUMENTS

EP  1 959 025  8/2008
EP  2 000 551  12/2008

(Continued)

OTHER PUBLICATIONS

Fan et al. ("Influence of Lanthanum on the Microstructure, Mechanical Property and Corrosion Resistance of Magnesium alloy", J Mater Sci (2006) 41:5409-5416).*

(Continued)

*Primary Examiner* — Weiping Zhu
(74) *Attorney, Agent, or Firm* — Fish & Richardson P.C.

(57) ABSTRACT

A bioerodible, implantable medical device that includes a supersaturated magnesium alloy. The magnesium alloy includes magnesium and at least one alloying element present in a concentration in excess of the equilibrium solid solubility concentration of the alloying element in hexagonal close-packed magnesium [at 25° C.].

18 Claims, 1 Drawing Sheet

U.S. PATENT DOCUMENTS

| | | |
|---|---|---|
| 2006/0241739 A1 | 10/2006 | Besselink |
| 2006/0271168 A1 | 11/2006 | Kleine |
| 2007/0003596 A1 | 1/2007 | Tittelbach |
| 2007/0020306 A1 | 1/2007 | Schultheiss |
| 2007/0135908 A1 | 6/2007 | Zhao |
| 2007/0142897 A1 | 6/2007 | Consigny |
| 2007/0142899 A1 | 6/2007 | Lootz |
| 2007/0148251 A1 | 6/2007 | Hossainy |
| 2007/0184083 A1 | 8/2007 | Coughlin |
| 2007/0191943 A1 * | 8/2007 | Shrivastava et al. ....... 623/11.11 |
| 2007/0219626 A1 | 9/2007 | Rolando |
| 2007/0225799 A1 | 9/2007 | Doty |
| 2007/0244541 A1 | 10/2007 | Schulman |
| 2007/0250155 A1 | 10/2007 | Simpson |
| 2007/0250158 A1 | 10/2007 | Krivoruchko |
| 2007/0254171 A1 | 11/2007 | Patel |
| 2007/0270940 A1 | 11/2007 | Doty |
| 2007/0270942 A1 | 11/2007 | Thomas |
| 2007/0299512 A1 | 12/2007 | Korzuschnik |
| 2008/0031765 A1 | 2/2008 | Gerold |
| 2008/0033530 A1 | 2/2008 | Zberg |
| 2008/0033531 A1 | 2/2008 | Barthel |
| 2008/0033533 A1 | 2/2008 | Borck |
| 2008/0033536 A1 | 2/2008 | Wittchow |
| 2008/0033537 A1 | 2/2008 | Tittelbach |
| 2008/0033538 A1 | 2/2008 | Borck |
| 2008/0033539 A1 | 2/2008 | Sternberg |
| 2008/0033576 A1 | 2/2008 | Gerold |
| 2008/0050413 A1 | 2/2008 | Horvers |
| 2008/0051335 A1 | 2/2008 | Kleiner |
| 2008/0051872 A1 | 2/2008 | Borck |
| 2008/0058923 A1 | 3/2008 | Bertsch |
| 2008/0090097 A1 | 4/2008 | Shaw |
| 2008/0103589 A1 | 5/2008 | Cheng |
| 2008/0175885 A1 | 7/2008 | Asgari |
| 2008/0177378 A1 | 7/2008 | Asgari |
| 2008/0188927 A1 | 8/2008 | Rohde |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1 | 8/2008 | Allen |
| 2008/0208313 A1 | 8/2008 | Yu |
| 2008/0208352 A1 | 8/2008 | Krivoruchko |
| 2008/0215129 A1 | 9/2008 | Venturelli |
| 2008/0215140 A1 | 9/2008 | Borck |
| 2008/0243230 A1 | 10/2008 | Lootz |
| 2008/0243234 A1 | 10/2008 | Wilcox |
| 2008/0243240 A1 | 10/2008 | Doty |
| 2008/0243242 A1 | 10/2008 | Kappelt |
| 2008/0262589 A1 | 10/2008 | Nagura |
| 2008/0269872 A1 | 10/2008 | Lootz |
| 2008/0306584 A1 | 12/2008 | Kramer-Brown |
| 2009/0005862 A1 | 1/2009 | Nakatani |
| 2009/0018648 A1 | 1/2009 | Wittchow |
| 2009/0024209 A1 | 1/2009 | Ozdil |
| 2009/0024210 A1 | 1/2009 | Klocke |
| 2009/0024211 A1 | 1/2009 | Wittchow |
| 2009/0030494 A1 | 1/2009 | Stefanadis |
| 2009/0030506 A1 | 1/2009 | Klocke |
| 2009/0030507 A1 | 1/2009 | Klocke |
| 2009/0035351 A1 | 2/2009 | Berglund |
| 2009/0043330 A1 | 2/2009 | To |
| 2009/0043374 A1 | 2/2009 | Nakano |
| 2009/0048660 A1 | 2/2009 | Adden |
| 2009/0062905 A1 | 3/2009 | Moore, Jr. |
| 2009/0069884 A1 | 3/2009 | Mueller |
| 2009/0076596 A1 | 3/2009 | Adden |
| 2009/0088831 A1 | 4/2009 | Goto |
| 2009/0088834 A1 | 4/2009 | Wang |
| 2009/0093871 A1 | 4/2009 | Rea |
| 2009/0131540 A1 | 5/2009 | Hiromoto |
| 2009/0164002 A1 | 6/2009 | Becher |
| 2009/0171452 A1 | 7/2009 | Yamamoto |
| 2009/0177273 A1 | 7/2009 | Piveteau |
| 2009/0182290 A1 | 7/2009 | Harder |
| 2009/0192571 A1 | 7/2009 | Stett |
| 2009/0192594 A1 | 7/2009 | Borck |
| 2009/0192595 A1 | 7/2009 | Nagura |
| 2009/0192596 A1 | 7/2009 | Adden |
| 2009/0198320 A1 | 8/2009 | Mueller |
| 2009/0204203 A1 | 8/2009 | Allen |
| 2009/0228037 A1 | 9/2009 | Rego |
| 2009/0240323 A1 | 9/2009 | Wilcox |
| 2009/0270979 A1 | 10/2009 | Adden |
| 2009/0274737 A1 | 11/2009 | Borck |
| 2009/0287302 A1 | 11/2009 | Thomas |
| 2009/0306766 A1 | 12/2009 | McDermott |
| 2009/0311300 A1 | 12/2009 | Wittchow |
| 2010/0010640 A1 | 1/2010 | Gerold |
| 2010/0016940 A1 | 1/2010 | Shokoohi |
| 2010/0023112 A1 | 1/2010 | Borck |
| 2010/0023116 A1 | 1/2010 | Borck |
| 2010/0028436 A1 | 2/2010 | Ohrlander |
| 2010/0034899 A1 | 2/2010 | Harder |
| 2010/0042206 A1 | 2/2010 | Yadav |
| 2010/0047312 A1 | 2/2010 | Wittchow |
| 2010/0049299 A1 | 2/2010 | Popowski |
| 2010/0049300 A1 | 2/2010 | Harder |
| 2010/0075162 A1 | 3/2010 | Yang |
| 2010/0076544 A1 | 3/2010 | Hoffmann |
| 2010/0076556 A1 | 3/2010 | Tomantschger |
| 2010/0082092 A1 | 4/2010 | Gerold |
| 2010/0087911 A1 | 4/2010 | Mueller |
| 2010/0087914 A1 | 4/2010 | Bayer |
| 2010/0087915 A1 | 4/2010 | Bayer |
| 2010/0087916 A1 | 4/2010 | Bayer |
| 2010/0092535 A1 | 4/2010 | Cook |
| 2010/0106243 A1 | 4/2010 | Wittchow |
| 2010/0119576 A1 | 5/2010 | Harder |
| 2010/0119581 A1 | 5/2010 | Gratz |
| 2010/0121432 A1 | 5/2010 | Klocke |
| 2010/0125325 A1 | 5/2010 | Allen |
| 2010/0131050 A1 | 5/2010 | Zhao |
| 2010/0131052 A1 | 5/2010 | Kappelt |
| 2010/0161031 A1 | 6/2010 | Papirov |

FOREIGN PATENT DOCUMENTS

| | | |
|---|---|---|
| EP | 2000551 A1 * | 12/2008 |
| JP | 2004-248886 | 9/2004 |
| WO | WO 03/002243 | 1/2003 |
| WO | WO 2007/013102 | 2/2007 |
| WO | WO 2007/035791 | 3/2007 |
| WO | WO 2007/079363 | 7/2007 |
| WO | 2007/107286 | 9/2007 |

OTHER PUBLICATIONS

Fan et al "Influence of lanthanum on the microstructure, mechanical property and corrosion resistance of magnesium alloy," *J Mater Sci*, 2006, 41:5409-5416.

Blawert et al., "Corrosion Properties of Supersaturated Magnesium Alloy Systems," *Materials Science Forum*, 2007, 539:1679-1684.

Magnesium Elektron, Elektron WE43, Datasheet: 467, dated 2005/2006.

Rokhlin, "The Regularities in the Mg-Rich Parts of the Phase Diagrams, Mechanical Properties of Magnesium Alloys with Individual Rare Earth Materials, 2007, 52:5-11 Phase Transformations, and Metals," *Arch. Mettallurgy Materials*, 2007, 52:5-11.

Authorized Officer Alina Zalfen, International Search Report and Written Opinion PCT/US2010/030332 mailed Jan. 27, 2011, 11 pages.

* cited by examiner

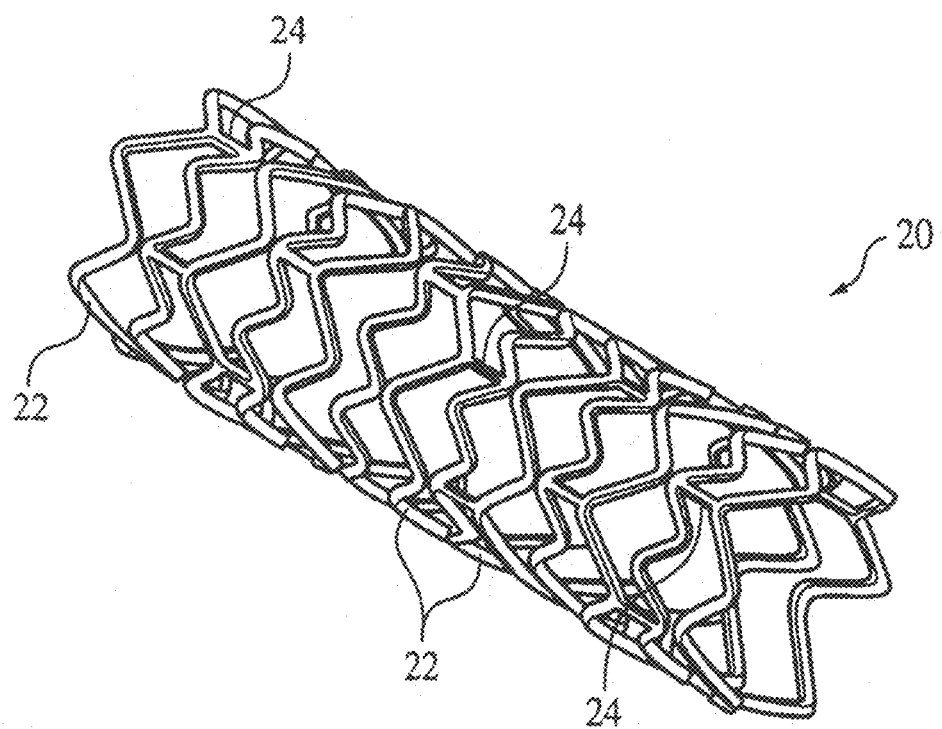

BIOERODIBLE, IMPLANTABLE MEDICAL DEVICES INCORPORATING SUPERSATURATED MAGNESIUM ALLOYS

TECHNICAL FIELD

This disclosure relates to bio-erodible, implantable medical devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with an implantable medical device such as an endoprosthesis. An endoprosthesis is typically a tubular member that is placed in a lumen in the body. Examples of endoprosthesis include stents, covered stents, and stent-grafts.

Endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

It is sometimes desirable for an implanted medical device such as an endoprosthesis to erode over time within the passageway. For example, a fully erodible endoprosthesis does not remain as a permanent object in the body, which may help the passageway recover to its natural condition. Bio-erodible medical devices can be formed from, e.g., a polymeric material, such as polylactic acid, or from a metallic material, such as magnesium, iron, or an alloy thereof.

It may be desirable for an implanted medical device such as a stent to erode relatively slowly at first, and then to accelerate after a period of time. When used for implantable medical devices, however, magnesium alloys generally erode too quickly.

SUMMARY

A bio-erodible, implantable medical device that includes a supersaturated magnesium alloy is described. The supersaturated magnesium alloy includes magnesium and at least one alloying element present in a concentration in excess of the equilibrium solid solubility concentration of the alloying element in hexagonal close-packed magnesium at 25° C. In some embodiments, the supersaturated magnesium alloy may have an average grain size less than 10 μm, and/or include no more than 0.0015 wt % iron, no more than 0.001 wt % nickel, and no more than 0.001 wt % Cu. In some embodiments, the supersaturated magnesium alloy includes more than one alloying element.

One class of suitable alloying elements includes rare earth elements from the lanthanide series. Specific examples include lanthanum, cerium, dysprosium, gadolinium, and combinations thereof. A second class of suitable alloying elements includes refractory metals selected from the group consisting of tungsten, molybdenum, niobium, tantalum, rhenium, and combinations thereof. A third class of suitable alloying elements includes transition metals selected from the group consisting of zirconium, chromium, hafnium, and combinations thereof. A fourth class of suitable alloying elements includes calcium.

In some embodiments, the implantable medical device includes a structural member, and the supersaturated magnesium alloy forms at least a portion of the structural member. In other embodiments, the supersaturated magnesium alloy is provided in the form of a coating on a surface of the structural member. It is also possible for the supersaturated magnesium alloy to form at least a portion of the structural member and to be provided as a coating on a surface of the structural member.

The bioerodible, implantable medical device may be in the form of an endoprosthesis such as a stent, an orthopedic implant, or a surgical staple.

The details of one or more embodiments are set forth in the accompanying drawings and the description below. Other features, objects, and advantages will be apparent from the description and drawings, and from the claims.

DESCRIPTION OF DRAWINGS

FIG. 1 illustrates an exemplary stent.

DETAILED DESCRIPTION

FIG. 1 illustrates an implantable bio-erodible medical device in the form of a stent 20. A medical device is bio-erodible if the medical device, or a portion thereof, exhibits substantial mass or density reduction, or chemical transformation, after it is implanted in a patient. Mass reduction can occur by, e.g., dissolution of the material that forms the medical device and/or fragmenting of the medical device. Chemical transformation can include oxidation/reduction, hydrolysis, substitution, and/or addition reactions, or other chemical reactions of the material from which the medical device, or a portion thereof, is made. The erosion can be the result of a chemical and/or biological interaction of the medical device with the body environment, e.g., the body itself or body fluids, into which it is implanted. The erosion can also be triggered by applying a triggering influence, such as a chemical reactant or energy to the medical device, e.g., to increase a reaction rate.

Stent 20 includes a tubular member defined by a plurality of bands 22 and a plurality of connectors 24 that extend between and connect adjacent bands 22. During use, bands 22 can expand from an initial, small diameter, compressed state to a larger diameter to contact stent 20 against a wall of a vessel, thereby maintaining the patency of the vessel. Connectors 24 provide stent 20 with flexibility and conformability that allow the stent to adapt to the contours of the vessel.

In order to render stent 20 bio-erodible upon implantation, all or portions of bands 22 and/or connectors 24 can be made of a supersaturated magnesium alloy. The supersaturated magnesium alloy includes magnesium and at least one alloying element present in a concentration in excess of the equilibrium solid solubility concentration of the alloying element in hexagonal close-packed magnesium at 25° C. Exemplary supersaturated magnesium alloys, and methods for producing them, are described in U.S. Pat. No. 6,908,516 to Hehmann et al., the entire disclosure of which is incorporated herein by reference.

Supersaturated magnesium alloys generally exhibit small average grain size (e.g., less than 10 μm) and a substantially homogeneous distribution of the alloying element(s) throughout the body of the alloy. This, in turn, can minimize creation of microgalvanic cells that enhance erosion rates. The supersaturated magnesium alloys offer the advantage, in the context of an implantable medical device such as a stent, of controlling the erosion behavior of the device so that it mimics a desired erosion profile. For example, in the case of a stent, use of the supersaturated magnesium alloy could achieve an erosion profile in which the stent erodes relatively slowly for a given period of time (e.g., for a time sufficient to allow endothelialization to take place), and then accelerates at the conclusion of this period.

The supersaturated magnesium alloy preferably has a very low impurity content. For example, the supersaturated magnesium alloy can have no more than 0.0015 wt % of iron (Fe), no more than 0.001 wt % of nickel (Ni), and no more than 0.001 wt % of copper (Cu). Minimizing the amounts of these elements can minimize the formation of microgalvanic couples that lead to enhanced erosion rates. For example, the erosion rate of a commercially available AZ91 magnesium alloy having about 0.005 wt % Fe is about 10 times higher than an ultra high pure AZ91 magnesium alloy having only about 0.0015 wt % Fe.

The supersaturated magnesium alloy can be obtained by rapid solidification processes. The rapid solidification processes establish a homogeneous distribution of an alloying element on an atomic length scale that goes well beyond the solubility limit of ingot metallurgy, thereby creating a supersaturation of the alloying element in the magnesium matrix. Representative examples of suitable rapid solidification processes include melt spinning, planar flow casting, and laser beam surface melting. Other examples include vapor phase processes such as vapor deposition, plasma sputtering, and magnetron sputtering. Further examples include pulsed laser deposition and nanocluster deposition. Specific examples are described in the aforementioned U.S. Pat. No. 6,908,516 to Hehmann et al.

One class of suitable alloying elements for preparing the supersaturated magnesium alloy includes rare earth elements from the lanthanide series. Specific examples include lanthanum, cerium, dysprosium, gadolinium, and combinations thereof. A second class of suitable alloying elements includes refractory metals selected from the group consisting of tungsten, molybdenum, niobium, tantalum, rhenium, and combinations thereof. A third class of suitable alloying elements includes transition metals selected from the group consisting of zirconium, chromium, hafnium, and combinations thereof. A fourth class of suitable alloying elements includes calcium. Specific examples, and amounts thereof, are described in the aforementioned U.S. Pat. No. 6,908,516 to Hehmann et al.

The supersaturated magnesium alloy may form all or a portion of a structural member of stent 20. The supersaturated magnesium alloy may be processed (e.g., by extrusion, rolling, forging, drawing, laser cutting, or other mechanical working) into various configurations, shapes, and/or dimensions. Regardless of the particular technique, however, the processing conditions are selected to maintain the supersaturated, non-equilibrium condition of the material. This includes avoiding the use of high temperatures that could cause the material to revert to its equilibrium condition. For example, the supersaturated magnesium alloy can be processed at temperatures lower than 140° C. for time periods shorter than 1 hour. The supersaturated magnesium alloy can also be processed to form a stent using a low temperature, femtosecond laser cutting process. Chemical etching could also be used.

The supersaturated magnesium alloy may also be in the form a coating over all or a portion of an external surface of a structural member of stent 20. For example, a rapid solidification process such as vapor sputtering may be used to apply a surface coating of a supersaturated magnesium alloy on top of a finished stent made out of a bio-erodible or non-bioerodible material. In some embodiments, a layer of a vapor deposited Mg-4.7% La alloy having a thickness of about 10 nm to about 1000 nm may be formed over a finished stent. Given a corrosion rate of about 1 μm/yr for the supersaturated Mg-4.7 wt % La alloy, a 200 nm surface layer may delay the corrosion of the underlying bulk by about 2 months. In some embodiments, a layer of a supersaturated Mg/La alloy having a thickness of about 100 nm to about 1 μm may be coated partly or entirely on a finished stent that includes an AZL alloy. The AZL alloy can be prepared by adding different amounts of pure lanthanum to an AZ91D alloy. The AZL alloy can include about 6-9 wt % of Al, about 0.5-0.8 wt % of Zn, about 0.5-1.5 wt % of La, and the balance as Mg. A high purity AZL alloy can include less than about 0.002 wt % of iron, less than about 0.002 wt % of copper, and less than about 0.002 wt % of nickel. In some embodiments, the AZL alloy has about 8.99 wt % of Al, about 0.709 wt % of Zn, about 1.064 wt % of La and the balance as Mg. Compared to the base AZ91D alloy, this AZL alloy exhibits an increase of about 21.1% in the ultimate tensile strength and an increase of about 101.2% in the elongation at break. Compared to other AZL alloys, this AZL alloy with about 1 wt % of La has the highest "pitting" potential and corrosion potential and the lowest corrosion current, and thus has the least tendency to localized corrosion.

Stent 20 may include a non-bioerodible material. Representative examples of suitable non-bioerodible materials include stainless steels, platinum enhanced stainless steels, cobalt-chromium alloys, nickel-titanium alloys, and combinations thereof. In some embodiments, stent 20 may include both bio-erodible and non-bio-erodible portions. For example, stent 20 could include a structural member having a non-bio-erodible metal body and a bio-erodible supersaturated magnesium alloy coating on a surface of the metal body.

Stent 20 may include a coating to provide a desired function. For example stent 20 may include a tie layer, a biocompatible outer coating, a radiopaque metal or alloy, a drug-eluting layer, or a combination thereof.

Stent 20 may include at least one releasable therapeutic agent, drug, or pharmaceutically active compound to inhibit restenosis, such as Paclitaxel and Everolimus, or to treat and/or inhibit pain, encrustation of the stent or sclerosing or necrosing of a treated lumen. The therapeutic agent, drug, or pharmaceutically active compound can be a genetic therapeutic agent, a non-genetic therapeutic agent, or cells. The therapeutic agent, drug, or pharmaceutically active compound can also be nonionic, or anionic and/or cationic in nature. Representative examples of suitable therapeutic agents, drugs, or pharmaceutically active compounds include anti-thrombogenic agents, antioxidants, anti-inflammatory agents, anesthetic agents, anti-coagulants, and antibiotics. In some embodiments, the therapeutic agent, drug, or a pharmaceutically active compound may be dispersed in a polymeric coating carried by the stent. In other embodiments, the therapeutic agent, drug, or a pharmaceutically active compound may be directly incorporated into the pores on the stent surface.

Stent 20 may have any desired shape and size (e.g., superficial femoral artery stents, coronary stents, aortic stents, peripheral vascular stents, gastrointestinal stents, urology stents, and neurology stents). Depending on the application, stent 20 can have an expanded diameter of about 1 mm to about 46 mm. For example, a coronary stent can have an expanded diameter of about 2 mm to about 6 mm. A peripheral stent can have an expanded diameter of about 5 mm to about 24 mm. A gastrointestinal and/or urology stent can have an expanded diameter of about 6 mm to about 30 mm. A neurology stent can have an expanded diameter of about 1 mm to about 12 mm. An abdominal aortic aneurysm stent and a thoracic aortic aneurysm stent can have an expanded diameter of about 20 mm to about 46 mm.

Stent 20 may be self-expandable, balloon-expandable, or a combination of self-expandable and balloon-expandable (e.g., as described in U.S. Pat. No. 5,366,504).

Stent 20 may have any suitable transverse cross-section, including circular and non-circular (e.g., polygonal such as square, hexagonal or octagonal).

Stent 20 can be implanted into a patient using a catheter delivery system. Representative catheter delivery systems are described in, for example, Wang, U.S. Pat. No. 5,195,969; Hamlin, U.S. Pat. No. 5,270,086; and Raeder-Devens, U.S. Pat. No. 6,726,712, the entire disclosure of each of those documents is incorporated herein by reference. Commercial examples of stents and stent delivery systems include Radius®, Symbiot® or Sentinol® system, available from Boston Scientific Scimed, Maple Grove, Minn.

Stents 20 may be a part of a covered stent or a stent-graft. For example, stent 20 can include and/or be attached to a biocompatible, non-porous or semi-porous polymer matrix made of polytetrafluoroethylene (PTFE), expanded PTFE, polyethylene, urethane, or polypropylene.

Stent 20 may be configured for vascular lumens. Stent 20 may also be configured for non-vascular lumens. For example, it can be configured for use in the esophagus or the prostate. Other lumens include biliary lumens, hepatic lumens, pancreatic lumens, urethral lumens and ureteral lumens.

In some embodiments, stent 20 may be formed by fabricating a wire that is covered with a supersaturated Mg/La coating and then knitting and/or weaving the wire into a tubular member.

A number of embodiments of the invention have been described. Nevertheless, it will be understood that various modifications may be made without departing from the spirit and scope of the invention. For example, In addition to stents, the supersaturated magnesium alloys may be used in implantable medical devices such as cochlear implants, bond screws, orthopedic implants, surgical staples, aneurism coils, and vascular closing device. Accordingly, other embodiments are within the scope of the following claims.

What is claimed is:

1. A bio-erodible, implantable medical device comprising a supersaturated magnesium alloy that includes magnesium and at least one alloying element present in a concentration in excess of the equilibrium solid solubility concentration of the alloying element in hexagonal close-packed magnesium at 25° C.

2. A bio-erodible, implantable medical device according to claim 1 wherein the supersaturated magnesium alloy has a microstructure characterized by an average grain size less than 10 μm.

3. A bio-erodible, implantable medical device according to claim 1 wherein the supersaturated magnesium alloy includes no more than 0.0015 wt. % iron, no more than 0.001 wt. % nickel, and no more than 0.001 wt. % Cu.

4. A bio-erodible, implantable medical device according to claim 1 wherein the alloying element is a rare earth element from the lanthanide series.

5. A bio-erodible, implantable medical device according to claim 4 wherein the rare element is selected from the group consisting of lanthanum, cerium, dysprosium, gadolinium, and combinations thereof.

6. A bio-erodible, implantable medical according to claim 1 wherein the alloying element is a refractory metal selected from the group consisting of tungsten, molybdenum, niobium, tantalum, rhenium, and combinations thereof.

7. A bio-erodible, implantable medical device according to claim 1 wherein the alloying element is a transition metal selected from the group consisting of zirconium, chromium, hafnium, and combinations thereof.

8. A bio-erodible, implantable medical device according to claim 1 wherein the alloying element is calcium.

9. A bio-erodible, implantable medical device according to claim 1 wherein the supersaturated magnesium alloy includes more than one alloying element.

10. A bio-erodible, implantable medical device according to claim 1 wherein the device includes a structural member and the supersaturated magnesium alloy forms at least a portion of the structural member.

11. A bio-erodible, implantable medical device according to claim 1 wherein the device includes a structural member and the supersaturated magnesium alloy is in the form of a coating on a surface of the structural member.

12. A bio-erodible, implantable medical device according to claim 1 wherein the alloying element is present in an amount no greater than about 5 wt. % based upon the total weight of the alloy.

13. A bio-erodible, implantable medical device according to claim 1 wherein the device comprises an endoprosthesis.

14. A bio-erodible, implantable medical device according to claim 13 wherein the endoprosthesis comprises a stent.

15. A bio-erodible, implantable medical device according to claim 1 wherein the device comprises an orthopedic implant.

16. A bio-erodible, implantable medical device according to claim 1 wherein the device comprises a surgical staple.

17. A bio-erodible, implantable medical device comprising a supersaturated magnesium alloy that includes magnesium and at least one alloying element present in a concentration in excess of the equilibrium solid solubility concentration of the alloying element in hexagonal close-packed magnesium at 25° C., wherein the device includes a structural member and the supersaturated magnesium alloy is in the form of a coating on a surface of the structural member, wherein the structural member comprises a high purity AZL alloy, and wherein the coating has an average thickness of about 100 nm to about 1 μm.

18. A bio-erodible stent comprising a supersaturated magnesium alloy that includes magnesium and at least one alloying element present in a concentration in excess of the equilibrium solid solubility concentration of the alloying element in hexagonal close-packed magnesium at 25° C., wherein the supersaturated magnesium alloy has a microstructure characterized by an average grain size less than 10 μm, and includes no more than 0.0015 wt. % iron, no more than 0.001 wt. % nickel, and no more than 0.001 wt. % Cu.

* * * * *

UNITED STATES PATENT AND TRADEMARK OFFICE
CERTIFICATE OF CORRECTION

PATENT NO. : 8,435,281 B2
APPLICATION NO. : 12/421928
DATED : May 7, 2013
INVENTOR(S) : Jan Weber It is certified that error appears in the above-identified patent and that said Letters Patent is hereby corrected as shown below:

1.) Title Page 2, Column 2, Item (56) - Other Publications, Entry 1, Line 1:
   Delete:
      "Fan et al"
   Insert:
      --Fan et al.,--.

2.) Title Page 2, Column 2, Item (56) - Other Publications, Entry 4, Lines 8-11:
   Delete:
      "Rokhlin, "The Regularities in the Mg-Rich Parts of the Phase Diagrams,
      Mechanical Properties of Magnesium Alloys with Individual Rare Earth Materials,
      2007, 52:5-11 Phase Transformations, and Metals," Arch. Metallurgy Materials,
      2007, 52:5-11."
   Insert:
      --Rokhlin, "The Regularities in the Mg-Rich Parts of the Phase Diagrams, Phase
      Transformations, and Mechanical Properties of Magnesium Alloys with Individual
      Rare Earth Metals," Arch. Metallurgy Materials, 2007, 52:5-11.--.

In the Claims:

3.) Column 6, Claim 6, line 12:
   Delete:
      "medical"
   Insert:
      --medical device--.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,435,281 B2 | Page 1 of 1 |
| APPLICATION NO. | : 12/421928 | |
| DATED | : May 7, 2013 | |
| INVENTOR(S) | : Weber | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this
Sixteenth Day of December, 2014

Michelle K. Lee
*Deputy Director of the United States Patent and Trademark Office*